United States Patent [19]
Hardester, III

[11] Patent Number: 5,438,978
[45] Date of Patent: Aug. 8, 1995

[54] DEVICE FOR ENHANCING MOISTURE CONTENT OF INSPIRED AIR IN A CLOSED RESPIRATORY SYSTEM

[75] Inventor: Walter E. Hardester, III, Mount Airy, Ga.

[73] Assignee: Weh, Inc., Decatur, Ga.

[21] Appl. No.: 125,474

[22] Filed: Sep. 23, 1993

[51] Int. Cl.6 .................. A61M 15/00; A61M 16/00; A62B 9/06; A62B 18/08
[52] U.S. Cl. .................. 128/201.13; 128/204.13; 128/204.17; 128/207.14
[58] Field of Search .......... 128/201.13, 204.17, 128/201.26, 201.27, 204.13, 207.14, 205.26

[56] References Cited

U.S. PATENT DOCUMENTS

| | | | |
|---|---|---|---|
| 2,228,502 | 1/1941 | Boothby | 128/201.13 |
| 3,107,669 | 10/1963 | Gross | 128/204.17 |
| 3,669,109 | 6/1972 | Cheffers et al. | 128/204.17 |
| 3,747,598 | 7/1973 | Cowans | 128/201.13 |
| 3,881,482 | 5/1975 | Lindholm | 128/201.13 |
| 3,954,920 | 5/1976 | Heath | 128/204.13 |
| 4,516,573 | 5/1985 | Gedeon | 128/201.13 |

FOREIGN PATENT DOCUMENTS

| | | | |
|---|---|---|---|
| 1022869 | 6/1983 | U.S.S.R. | 128/204.17 |
| 8401720 | 5/1984 | WIPO | 128/204.17 |
| 8503880 | 9/1985 | WIPO | 128/204.17 |

Primary Examiner—Kimberly L. Asher
Attorney, Agent, or Firm—Bernstein & Associates

[57] ABSTRACT

A hollow, elongated shaft (20) containing a layer of porous material (30) that is capable of retaining moisture is designed to fit within the airway (13) of the mouthpiece (11) of a closed respiratory system to receive water vapor from expired air and allow the water vapor to be taken up by inspired air.

4 Claims, 1 Drawing Sheet

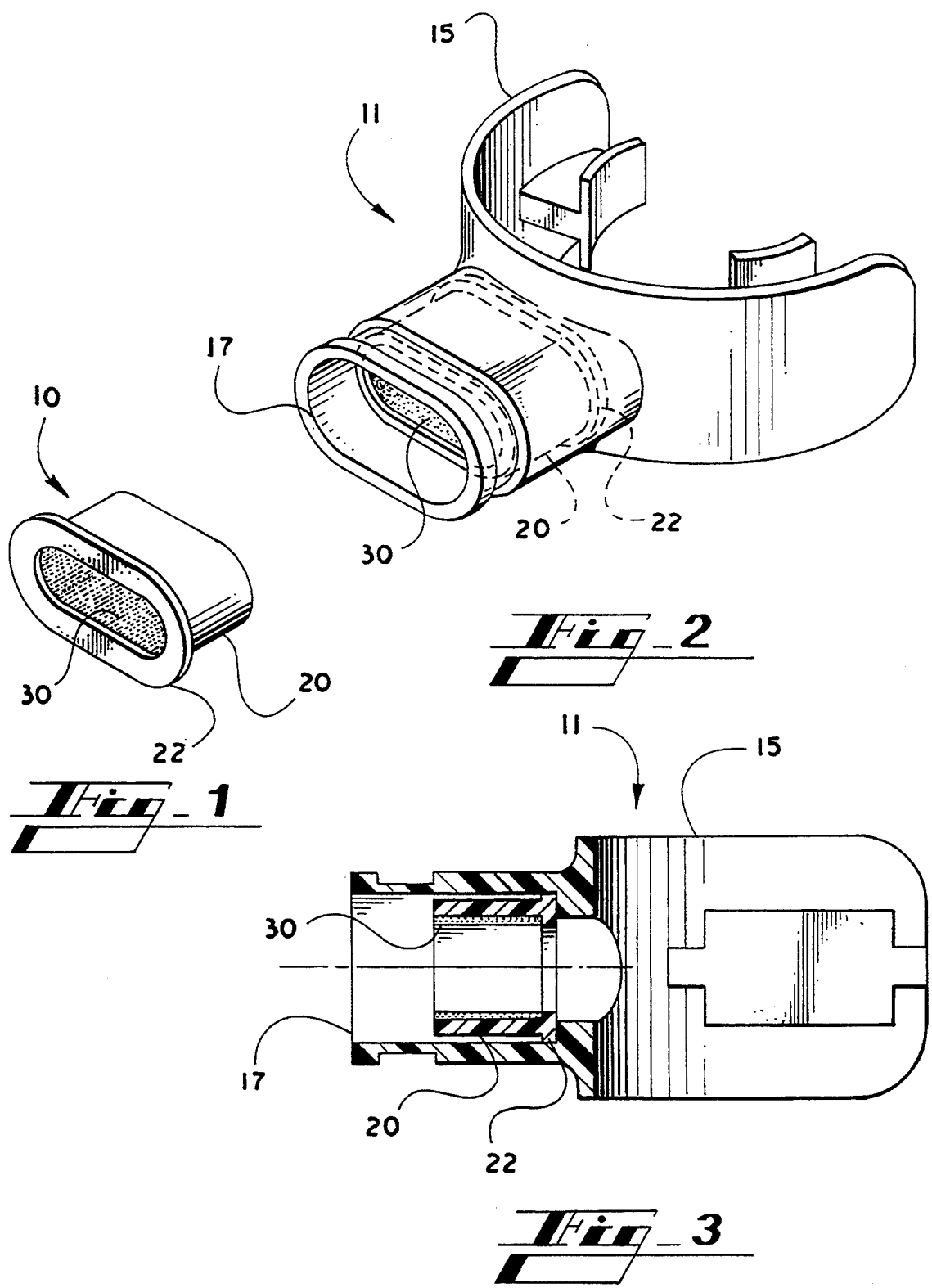

DEVICE FOR ENHANCING MOISTURE CONTENT OF INSPIRED AIR IN A CLOSED RESPIRATORY SYSTEM

TECHNICAL FIELD OF THE INVENTION

The present invention relates to closed respiratory systems, such as a scuba diving tank, regulator and mouthpiece, and more particularly to a device for enhancing moisture content of inspired air in a closed respiratory system.

BACKGROUND OF THE INVENTION

Closed respiratory systems are used when it is not possible for an individual to breath air normally. An example of a closed respiratory system is the air tank, air hose, regulator and mouthpiece used by a scuba diver to breath underwater. A problem for users of the closed system is that air that is inhaled from an air tank is generally devoid of moisture. Moisture is needed in inhaled air to prevent the user's mouth, throat and lungs from becoming unnecessarily dry and to aid in the respiratory process in general. Lack of moisture in inspired air may cause the user of the closed respiratory system to become dehydrated and uncomfortable. Dehydration and discomfort can lead to a more limited use of the respiratory system than desired and may cause the user to be distracted from the task or environment to which attention should be focused. Excessive dryness of the mouth and upper airways can also cause the user to inhale and exhale in an undesirable manner in an attempt to compensate for the dryness. Thus, it can be appreciated that it would be desirable to have a means for enhancing the moisture content of inspired air in a closed respiratory system. Because exhaled air contains moisture, it can be appreciated that it would also be desirable to utilize moisture in expired air in a closed respiratory system to enhance the moisture content of inspired air in the system.

SUMMARY OF THE INVENTION

It is an object of the invention to provide a means for enhancing the moisture content of inspired air in a closed respiratory system.

It is a further object of the invention to provide a means to utilize moisture in expired air in a closed respiratory system to enhance the moisture content of inspired air in the system.

It is also an object of the invention to provide an insert that may be used in standard scuba diving equipment to utilize moisture in expired air in a scuba diving respiratory system to enhance the moisture content of inspired air in the system.

In the present invention, a hollow, elongated shaft contains a layer of porous material that is capable of retaining moisture and is designed to fit within the airway of the mouthpiece of a closed respiratory system to receive water vapor from expired air and allow the water vapor to be taken up by inspired air.

Other aspects, objects, features, and advantages of the present invention will become apparent to those skilled in the art upon reading the detailed description of preferred embodiments.

BRIEF DESCRIPTION OF THE DRAWINGS

FIG. 1 is an isometric illustration of a device for enhancing moisture content of inspired air in closed respiratory system according to a preferred embodiment of the invention.

FIG. 2 is a reverse isometric illustration of the device shown in FIG. 1, shown embedded in the mouthpiece of scuba diving equipment.

FIG. 3 is a sectional view of the device show in FIGS. 1 and 2 inserted in the mouthpiece of scuba diving equipment.

DETAILED DESCRIPTION OF PREFERRED EMBODIMENTS OF THE INVENTION

While the specification concludes with claims particularly pointing out and distinctly claiming the subject matter which is regarded as the present invention, the invention will now be described with reference to the following description of embodiments taken in conjunction with the accompanying drawings. The same reference numerals are used to refer to like features throughout the drawings.

The invention can be used with any closed respiratory system in which inspired air is lacking in moisture content and the same air passageway is used for the flow of both inspired and expired air. In the preferred embodiment illustrated in FIGS. 1, 2 and 3 and described herein, the device is an insert 10 for use with the mouthpiece 11 of scuba equipment. Scuba diving equipment, consisting primarily of an air tank, air hoses, an air regulator and a mouthpiece attached to the air regulator is a closed respiratory system that enables a user to breath under water. A firefighter's air-breathing apparatus is another example of a closed respiratory system. Referring first to FIG. 1, the insert 10 is a hollow, elongated shaft 20 containing a layer of moisture-exchanging material. Referring now also to FIGS. 2 and 3, the insert 10 is designed to fit within the airway of the scuba mouthpiece 11. The mouthpiece 11 consists of an airway conduit 13 terminating in a mouth adapter 15 which is held in the diver's mouth. Air is received by and exhaled by the diver through the open end 17 of the mouthpiece 11. The shaft 20 of the insert 10 has a cross-sectional area slightly smaller than the interior cross-sectional area of the airway 13 of the mouthpiece 11. The shaft 20 of the insert 10 is thus enabled to be snugly fitted into the mouthpiece 11. A flange 22 at the end of the insert 20 prevents the insert 10 from being pushed through the adapter 15 end of the mouthpiece 11. The moisture-exchanging material 30 which covers the inner surface of the shaft 20 is a layer of porous material 30 which has the ability to receive and retain water vapor deposited by expired air and release retained water vapor to inspired air. A suitable moisture-exchanging material 30 having this property is reticulated polyurethane. Other types of foam-like or cellular material that exhibit these same moisture-exchanging properties may also be used. The shaft 20 may be made of a plastic.

The insert 10 is inserted in the mouthpiece 11 between the mouth of a user and the point at which exhaled air exits the closed respiratory system (in scuba diving equipment, exhaled air exits the system through the regulator). As air is exhaled by the user, water vapor is deposited in the porous material 30. When vapor-deficient air from the air tank of the scuba diver is inspired, the inspired air passes through the insert 10 and takes on the deposited vapor.

The insert 10 can be inserted by bending back the mouth adapter 15 portion of the mouthpiece 11 and pushing the insert into place. The insert 10 is a cartridge that may be changed daily or as needed.

As should be apparent from the foregoing specification, the invention is susceptible of being modified with various alterations and modifications which may differ from those which have been described in the preceding specification and description. Accordingly, the following claims are intended to cover all alterations and modifications which do not depart from the spirit and scope of the invention.

What is claimed is:

1. An insert device for enhancing moisture content of inspired air in a closed respiratory system, comprising:
   a support means for providing a substantially unobstructed passageway for passage of a longitudinal flow of air comprising an elongated, open, hollow shaft open at both ends adapted for insertion into an airway of a mouthpiece of a closed respiratory system, said support means also having an outer wall and a generally smooth, flat inner wall; and
   a hollow, elongated, cylindrical layer of porous material having a thickness and a substantially circular cross-section, an inner surface and an outer surface, said outer surface being attached to and lining said inner wall of said support means, said layer of porous material not filling the passageway of said support means, expired air and moisture passing through said support means passageway, said porous material receiving and retaining water vapor from expired air passing through said porous material, said inner wall of said support means preventing water vapor from passing completely through said layer of porous material, said layer of porous material subsequently releasing the retained water vapor to inspired air passing through said support means passageway.

2. The invention of claim 1, wherein said porous material is a foam material.

3. The invention of claim 1, wherein said porous material is reticulated polyurethane.

4. The insert device of claim 1, further comprising a flange extending from one end of said support means.

\* \* \* \* \*